(12) United States Patent
Huston et al.

(10) Patent No.: US 7,105,638 B1
(45) Date of Patent: Sep. 12, 2006

(54) PRODUCT AND PROCESS FOR THE PRODUCTION, ISOLATION, AND PURIFICATION OF RECOMBINANT POLYPEPTIDE

(75) Inventors: James S. Huston, Newton, MA (US); Marc F. Charette, West Roxbury, MA (US); Charles M. Cohen, Medway, MA (US); Roberto Crea, Boston, MA (US); Peter C. Keck, Millbury, MA (US); Hermann Oppermann, Medway, MA (US); David C. Rueger, West Roxbury, MA (US); Richard J. Ridge, Acton, MA (US)

(73) Assignee: Micromet AG, Munich (DE)

( * ) Notice: Subject to any disclaimer, the term of this patent is extended or adjusted under 35 U.S.C. 154(b) by 0 days.

(21) Appl. No.: 08/014,096

(22) Filed: Feb. 4, 1993

Related U.S. Application Data

(60) Continuation of application No. 07/661,070, filed on Feb. 26, 1991, now abandoned, which is a division of application No. 07/462,297, filed on Dec. 28, 1989, now Pat. No. 5,013,653, which is a continuation of application No. 07/028,484, filed on Mar. 20, 1987, now abandoned.

(51) Int. Cl.
 *C07K 16/46* (2006.01)
(52) U.S. Cl. .................. 530/387.3; 435/69.7; 536/23.4
(58) Field of Classification Search ............... 435/69.7; 530/350, 412; 536/27
See application file for complete search history.

(56) References Cited

U.S. PATENT DOCUMENTS

| | | | |
|---|---|---|---|
| 4,366,246 A | 12/1982 | Riggs | 435/68 |
| 4,425,437 A | 1/1984 | Riggs | 435/317 |
| 4,431,739 A | 2/1984 | Riggs | 435/253 |
| 4,512,922 A | 4/1985 | Jones | 260/112 |
| 4,530,787 A | 7/1985 | Shaked | 260/112 |
| 4,543,329 A | 9/1985 | Daum et al. | 435/69 |
| 4,563,424 A | 1/1986 | Riggs | 435/71 |
| 4,599,197 A | 7/1986 | Wetzel | 530/405 |
| 4,620,948 A | 11/1986 | Builder | 530/419 |
| 4,743,679 A * | 5/1988 | Cohen et al. | 530/350 |
| 4,751,180 A * | 6/1988 | Cousens et al. | 435/69.7 |
| 4,766,224 A | 8/1988 | Rausch | 530/412 |

FOREIGN PATENT DOCUMENTS

| | | |
|---|---|---|
| EP | 0035384 | 9/1981 |
| EP | 0047600 | 3/1982 |
| EP | 0070675 | 1/1983 |
| EP | 0117058 | 8/1984 |
| EP | 0117059 | 8/1984 |
| EP | 2140810 | 12/1984 |
| EP | 0150126 | 7/1985 |
| EP | 0161937 | 11/1985 |
| EP | 0163573 | 12/1985 |
| EP | 0207044 | 12/1986 |
| WO | 83 04030 | 11/1983 |
| WO | 84 03103 | 8/1984 |
| WO | 8403103 | * 8/1984 |
| WO | 84 04756 | 12/1984 |
| WO | 85 03079 | 7/1985 |

OTHER PUBLICATIONS

A.L. Lehninger, "Biochemistry", 1978, Worth Publishers, pp. 130 to 131.*
Chou, P.Y., & Fasman G. D. 1978, Ann. Rev. Biochem., 47:251-76, Empirical Predications . . .
Welply et al., 1981, Journal Biolog. Chem., 256(13) 6811-6816, "B-Galachosidase a-Complementation".
Kabsch, W. et al., 1983, FEBS Letters, 155(2) 179-182.
King, J., Apr. 10, 1989, Chem & Eng. News, 32-54.
Brewer & Sassenfeld, "The Purification of Recombinant Proteins Using C-Terminal Polyargineni Fasions" (1985) 119-122.
"Gene Fusion Vectors Based on Gene..Protein A", Gene, 1983 23:369-378.
Use of Gene Fusions and Protein . . . The Replication Initiator . . . R6K, Proc. Natl. Acad. Sci. 1983, 80-6848-6852.
A Polypeptide Fusion . . . for the Purification of Recombinant Proteins, Biotech., 1984, 76-81.
"Generation of B-Globin..E coli", Nature 1984 309:810-812.
"Rapid Purification of a Cloned Gene Product", Proc. Natl. Acad. Sci. U.S.A., 1984 81:4692-4696.

* cited by examiner

*Primary Examiner*—John Ulm
(74) *Attorney, Agent, or Firm*—Fish & Richardson P.C.

(57) ABSTRACT

Disclosed is a method for the isolation and purification of polypeptides expressed in host cells by recombinant DNA techniques. A fused polypeptide is produced containing a desired polypeptide fused to additional amino acids. The additional amino acids define a leader sequence having properties exploitable in purification, a hinge region, and a cleavage site. The hinge region is cysteine-free and has a secondary structure which serves to expose the cleavage site to a selected endopeptidase. The method of the invention involves the production of a fused polypeptide which may be efficiently isolated by exploiting the properties of the leader sequence, and then efficiently cleaved at the cleavage site in an appropriate aqueous environment by virtue of the influence of the hinge on the cleavage agent/cleavage site reaction and other properties of the fused polypeptide.

18 Claims, 3 Drawing Sheets

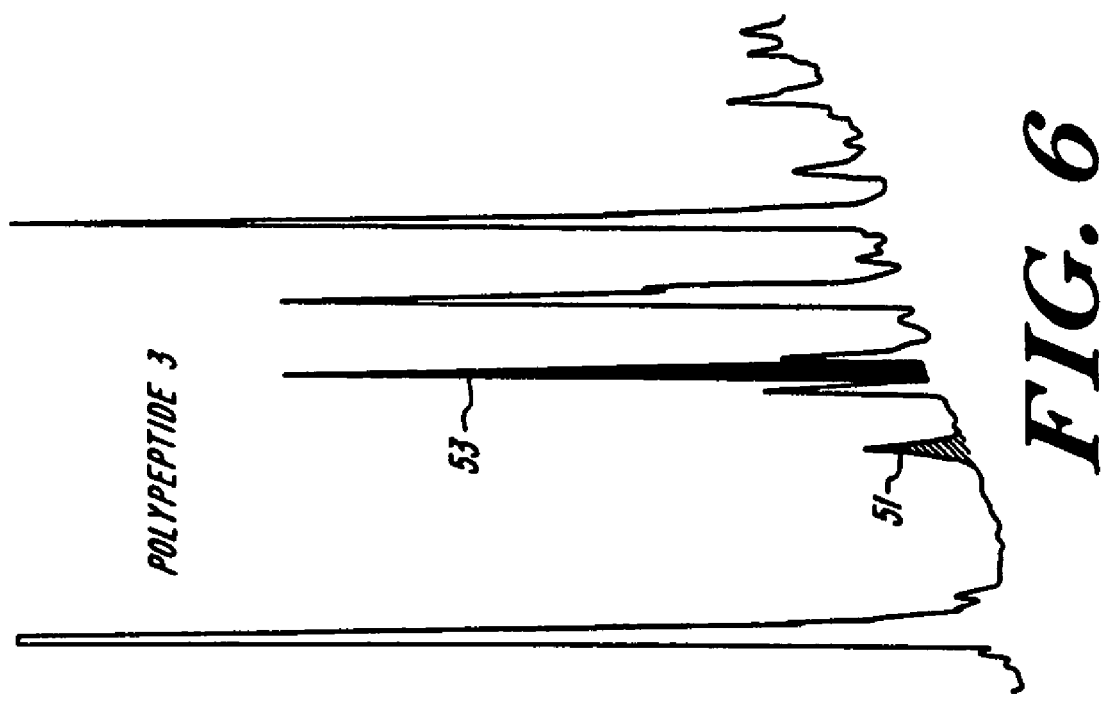
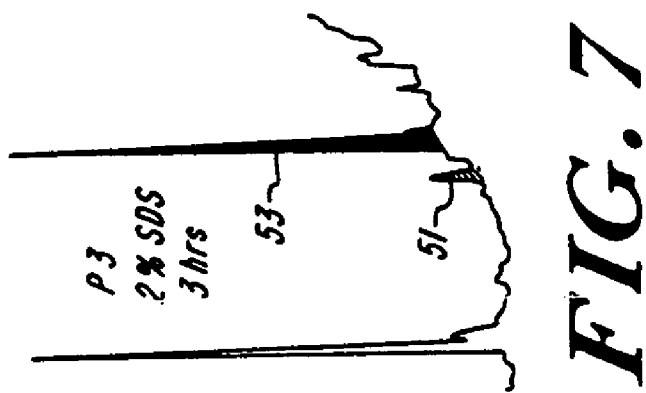

PRODUCT AND PROCESS FOR THE PRODUCTION, ISOLATION, AND PURIFICATION OF RECOMBINANT POLYPEPTIDE

This is a continuation of application(s) Ser. No. 07/661,070 filed on Feb. 26, 1991 now abandoned; which is a divisional of Ser. No. 07/462,297 filed on Dec. 28, 1989; now U.S. Pat. No. 5,013,653 which is a continuation of Ser. No. 07/028,484 filed on Mar. 20, 1987 now abandoned.

BACKGROUND

This invention relates to the isolation and purification of polypeptides produced using genetic engineering techniques. More particularly, it relates to the design of genetically engineered fused polypeptides and the isolation and purification of target polypeptides therefrom by cleavage.

Advancements in recombinant DNA technology permitting foreign genes to be incorporated into various cells have made possible the expression of a product foreign to the cell. The molecular biology governing the expression of recombinant DNA places a variety of constraints on the form of polypeptides or proteins produced in the host organism. For instance, intracellular enzymes will often degrade the protein of interest, and it may be difficult to separate from other materials expressed by or comprising the structural materials of the host organism.

The development of fusion or hybrid polypeptide methodology has facilitated the protection, isolation, and purification of genetically engineered polypeptides and overcomes some of these constraints. Protection from intracellular degradation can be accomplished by fusing a sequence of amino acids to the target protein to avoid digestion by enzymes within the cell. A fusion product can be engineered to be secreted from the host into the growth medium by fusing a signal peptide to the target. In addition, the hybrid can be designed to facilitate isolation and purification if the desired protein is fused to a polypeptide having characteristics exploitable in purification. The fusion product is prepared by engineering the gene coding for the protein of interest in reading frame with a DNA sequence of a polypeptide other than the protein of interest. For instance, DNA specifying a positively charged peptide or other molecule can be fused to the DNA encoding the target protein, allowing the protein product to bind strongly to negatively charged ion-exchange or affinity matrices.

The production of proteins with fusion methodology is also faced with constraints. For example, the material fused to the target protein must not permanently interfere with the biological activity of the target protein, and efficient cleavage of the fused material to obtain purified target protein can be difficult to achieve. Often only some fraction of the fusion protein is properly cleaved, and therefore existing methods provide low purification efficiency. Furthermore, the cleavage agent may cleave at several locations resulting in product loss and the production of contaminating fragments.

Fusion methodology has been discussed at length in the prior art. For example, European Patent Application No. 0047600 is understood to disclose a process for synthesizing bovine growth hormone by producing a fusion protein and purifying the growth hormone from the culture medium of the host organism. Other proteins have been produced through fusion techniques.

Generally, the prior art teaches that genetic material encoding a cleavage site can be incorporated between the DNA encoding the desired protein and the DNA encoding the additional fused material. Expression yields a precursor protein comprising the amino acid sequence of the target polypeptide linked to one or more peptides defining a selected cleavage site and another amino acid sequence. EPO 0035384 discloses the use of fusion proteins having specific cleavage sites incorporated in their structures which facilitate purification of expression products. EPO 0161937 discloses a recombinant fusion protein including a DNA sequence encoding a site specifically cleavable by blood coagulation Factor Xa. EPO 0163573 is understood to disclose a nucleotide sequence inserted into a plasmid expression vector which codes for an amino acid sequence specifically recognizable by the proteolytic enzyme renin.

The fusion product can comprise a moiety designed to facilitate isolation of the desired product. For instance, PCT/84/03103 discloses a DNA sequence coding for the protein of interest linked to a DNA sequence coding for protein A or another macromolecule capable of binding to the constant region of immunoglobulins. The fusion protein is purified by adsorption of protein A to immobilized IgG. In addition, a cleavage site can be incorporated between the protein A fragment and the protein of interest. The target protein can then be cleaved from the remainder of the fused product adsorbed to the IgG carrier. U.S. Pat. No. 4,431,739 also describes a method of expressing a precursor protein containing a desired protein, an additional polypeptide, and a selective cleavage site adjacent the desired protein.

Recombinant technology potentially can provide useful proteins in large quantities in easily purifiable form. Large quantities of pure proteins are needed for clinical use and research. Therefore inexpensive, efficient, high yielding production methods are necessary. What is needed is an efficient method for the purification of polypeptides produced through recombinant DNA which is generally independent of the properties of the cloned protein. This would enable adaptation of the procedure to the production of any desired protein. What is also needed is a method for increasing the yield of the purified proteins made using the fusion technology.

It is an object of this invention to provide a procedure for the production, isolation, and purification of genetically engineered proteins. Another object is to provide a method for obtaining recombinant protein of interest in improved yields. Another object is to provide a method which can be adapted to any polypeptide of interest which can be coded for and expressed by a host organism. Still another object is to provide such a procedure which is both efficient and inexpensive.

These and other objects of the invention will be apparent from the description, drawing, and claims that follow.

SUMMARY OF THE INVENTION

This invention provides a method for the preparation, isolation, and purification of a desired recombinant protein. The method can provide high yields of a purified protein of interest. Broadly, the invention features in its various aspects novel recombinant DNAs, the fused polypeptides encoded by the recombinant DNAs, as well as methods for production of a protein involving these novel agents.

In accordance with the invention, recombinant DNAs are produced by generally known techniques as disclosed herein. The recombinant DNA is designed to be expressed in a procaryotic or eucaryotic organism and to encode a fused polypeptide. The fused polypeptide consists of a first sequence of amino acids which define a "hook region", so called because one of its primary functions is to act as a hook to extract the fused protein from diverse other proteins produced by the transformant. The hook region comprises a leader sequence, a "hinge region" (see below), and an amino acid or amino acid sequence which defines a cleavage site recognizable and cleavable by a selected cleavage agent, preferably an endopeptidase. The fused polypeptide also encodes a second sequence of amino acids linked to the cleavage site and encoding the protein of interest, called herein the "target". The cleavage site, when acted on by the cleavage agent, permits separation of the first sequence from the second.

The hinge region is a sequence of amino acids which serve to promote efficient cleavage by the cleavage agent at the cleavage site. It is designed to promote cleavage preferentially at the cleavage site when the fused polypeptide is treated with the cleavage agent in an appropriate environment.

The hinge can take many different forms. Its design involves selection of amino acid residues (and a DNA fragment encoding them) which impart to the region of the fused protein about the cleavage site an appropriate polarity, charge distribution, and stereochemistry which, in the aqueous environment where the cleavage takes place, efficiently exposes the cleavage site to the cleavage agent in preference to other potential cleavage sites that may be present in the fused polypeptide, and/or to improve the kinetics of the cleavage reaction. In specific cases, the amino acids of the hinge are selected and assembled in sequence based on their known properties, and then the fused polypeptide sequence is expressed, tested, and altered for empirical refinement.

The hinge region and preferably the leader as well are free of cysteine so that disulfide bonds cannot form between it and the target protein. This enables the cleavage reaction to be conducted under conditions in which the target protein assumes its tertiary conformation, and may be held in this conformation by intramolecular disulfide bonds. It has been discovered that in these conditions access of the protease to potential cleavage sites which may be present within the target protein is hindered.

The hinge region may comprise an amino acid sequence which includes one or more proline residues. This allows formation of a substantially unfolded molecular segment, and is particularly useful when the leader sequence forms a helix or other secondary structure which might adversely influence access of the endopeptidase to the cleavage site. The hinge region can also contain an amino acid sequence which minimizes interactions of the target protein, leader, cleavage site, or other proteins with the hinge region, physicochemically described as the formation of a random coil within the hinge, when the fused protein is dispersed in aqueous solution. Aspartic acid, glutamic acid, arginine, lysine, serine, and threonine, residues which maximize ionic interactions are preferred for this purpose. They should be present in amounts and/or in sequence which renders the moiety comprising the hinge water soluble.

The leader sequence of the hook region may be a known leader. Its primary function is to promote high levels of expression in a specific host, in accordance with the teachings of the prior art. In one preferred embodiment, the leader comprises an amphiphilic helix of the type described herein. In addition, or instead, the hook region can consist of an amino acid sequence defining a binding site which interacts with a selected receptor exogenous to the host organism. The binding site permits isolation of the fused polypeptide prior to cleavage and final purification.

For instance, the binding site may consist of protein A or fractions thereof, which binds to immunoglobulins immobilized on a support matrix. Preferred binding sites of the precursor fused protein include B-galactosidase, and chloramphenicol acetyltransferase.

In preferred embodiments, the cleavage site is immediately adjacent the target polypeptide and comprises one or a sequence of amino acids exclusive of any one or sequence found in the target polypeptide. In some cases, potential cleavage sites in the target protein can be removed by substituting amino acids of similar chemical structure for an amino acid recognized as a cleavage site without significantly altering the bioproperties of the target. When all such potential cleavage sites are removed from the target polypeptide, the cleavage agent recognizes only the built-in linking cleavage site, and unwanted cleavage of the product is eliminated. It is further preferred for the cleavage site to comprise a unique sequence of amino acids in the entirety of the fused polypeptide product. It may be preferred to conduct the cleavage under non-reducing and non-denaturing conditions so that the target polypeptide has tertiary structure and may be disulfide bonded. In this circumstance, any potential cleavage sites the target may contain is likely to be relatively unaffected by the selected proteolytic cleavage agent. In another circumstance, where disulfide bonds are close to the cleavage site, reduction can facilitate cleavage. This is useful when the target protein is not required to be folded to protect it from the cleavage agent.

The cleavage site preferably is designed for cleavage by a specific selected agent. Endopeptidases are preferred, although non-enzymatic cleavage agents may be used. Many useful cleavage agents, for instance, cyanogen bromide, dilute acid, trypsin, S. aureus V-8 protease (V-8 protease), post proline cleaving enzyme, blood coagulation Factor Xa, enterokinase, and renin, recognize and preferentially or exclusively cleave particular cleavage sites. The currently preferred cleavage agent is V-8 protease, which cleaves at the C-terminal side of an exposed Glu residue.

The method of the invention comprises culturing an organism containing and capable of expressing a recombinant DNA encoding a fused polypeptide as described above. The expressed fused polypeptide product is exposed to a cleavage agent that recognizes the cleavage site made preferentially accessible by the stereochemistry, polarity, and/or charge distribution of the hinge region. Acting on the cleavage site, the cleavage agent cleaves the target polypeptide from the remainder of the fused polypeptide. The target polypeptide can then be separated from the remainder of the fused polypeptide by conventional purification techniques. On the other hand, if, as preferred, the precursor protein is bound to a receptor on a support matrix prior to cleavage, the cleaved target protein need only be purified from the cleavage agent as the remainder of the fused product remains bound to the support matrix.

Prior to cleavage, the fused polypeptide may be concentrated or isolated by the exploitation of the preselected properties of the leader sequence section of the hook. For instance, the solubility properties imparted to the fused polypeptide by the leader sequence can serve as the basis for separation by promoting the intracellular formation of inclusion bodies which can be retrieved to result in a fused protein-rich fraction well suited for subsequent purification.

In many instances, the existence of an amino acid or amino acid sequence in the target polypeptide which may also be cleaved by the selected cleavage agent cannot readily be avoided. In these cases, in accordance with the invention, unwanted cleavage is nevertheless greatly reduced relative to fused proteins of the prior art, because of the influence of the hinge.

Where cleavage can occur in the target polypeptide at a significant but lesser rate than the cleavage reaction rate at the built-in cleavage site, a recycle method may be used to enhance cleavage. Specifically, prior to termination of the cleavage reaction, the cleaved target polypeptide is separated from the remainder of the reaction mixture such that the second cleavage cannot occur. The remainder of the reaction mixture is then reexposed to the cleavage agent to harvest additional amounts of product, and this sequence of steps is repeated as often as desired.

In another aspect of the invention, the process is used to produce bioactive analogs of glutamic acid-containing target proteins. The DNA sequence encoding the protein is altered by known techniques to replace Glu residues present in the protein's native form with an Asp residue. Often, because of the structural similarity of aspartic and glutamic acid, the tertiary structure and activity of the analog will be very close to the native protein. A Glu residue is then employed as a cleavage site, preferably but not necessarily attached to a hinge of the type disclosed above, and a leader sequence. The expressed fused polypeptide is then treated with V-8 protease under conditions in which the carboxy side of the Glu is cleaved, e.g., in alkaline conditions in the presence of acetate or carbonate ion.

The methods of the present invention have general utility, and can be tailored in accordance with the teachings disclosed herein for use with any polypeptide of interest which can be encoded and expressed by a gene inserted into a host.

BRIEF DESCRIPTION OF THE DRAWINGS

FIGS. 4, 5, and 6 are HPLC chromatograms showing resolution of intact, 53 amino acid epidermal growth factor (EGF) and a truncated 51 amino acid analog of EGF, produced by cleaving with V-8 protease 1) a recombinant fusion protein having no hinge region (FIG. 4) and 2) two fusion proteins embodying the invention having hinge regions (FIGS. 5 and 6);

FIG. 7 is an HPLC chromatogram showing resolution of the 53 and 51 amino acid EGF molecules produced by cleaving the fusion protein of the invention with V-8 protease in the presence of 2% sodium dodecyl sulfate.

DESCRIPTION

The processes for manipulating, amplifying, and recombining DNA which encode amino acid sequences of interest are generally well known in the art, and therefore, not described in detail herein. Methods of identifying and isolating genes encoding proteins of interest, or for constructing such genes, are well understood and developed. These processes are described in the patent and other literature. See, for example, U.S. Pat. No. 4,431,739. In general, the methods involve selecting genetic material coding for amino acids which define the polypeptide of interest according to the genetic code.

Accordingly, the DNA construction principle disclosed herein can be exploited using known construction techniques involving the use of various restriction enzymes which make sequence specific cuts in DNA to produce blunt ends or cohesive ends, DNA ligases, techniques enabling enzymatic addition of sticky ends to blunt-ended DNA, construction of synthetic DNAs by assembly of short oligonucleotides, cDNA synthesis techniques, and synthetic probes for isolating genes having a particular function. Various promoter sequences and other regulatory DNA sequences used in achieving expression, and various types of host cells are also known and available. Conventional transfection techniques, and equally conventional techniques for cloning and subcloning DNA are also useful in the practice of this invention and known to those skilled in the art. Various types of vectors may be used such as plasmids and viruses including animal viruses and bacteriophages. The vectors may exploit various marker genes which impart to a successfully transfected cell a detectable phenotypic characteristic that can be used to identify which of a family of cells has successfully incorporated the recombinant DNA of the vector.

The production of various proteins of interest has heretofore been achieved by expressing fused protein which is collected, purified, and then cleaved to remove the extraneous portion of the molecule. This invention constitutes an improvement and unobvious refinement of this general method. The process of the invention generally involves engineering a recombinant DNA which, upon expression in a suitable host, produces a fused polypeptide. The fused polypeptide, among other advantageous properties, may be efficiently cleaved by virtue of a relatively short polypeptide moiety disposed about the cleavage site 14' included at an appropriate location in its structure, and by virtue of other properties of the molecule discussed below. The fused polypeptide also preferably includes a polypeptide moiety in its leader designed specifically to facilitate its purification.

Figure 1:
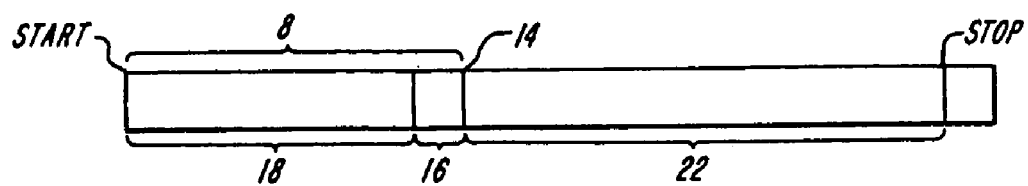
FIG. 1 is a schematic representation of the recombinant DNA of the invention containing DNA encoding a hook comprising a cleavage site, a hinge region, and leader sequence, linked to DNA encoding a target polypeptide.
Figure 2:
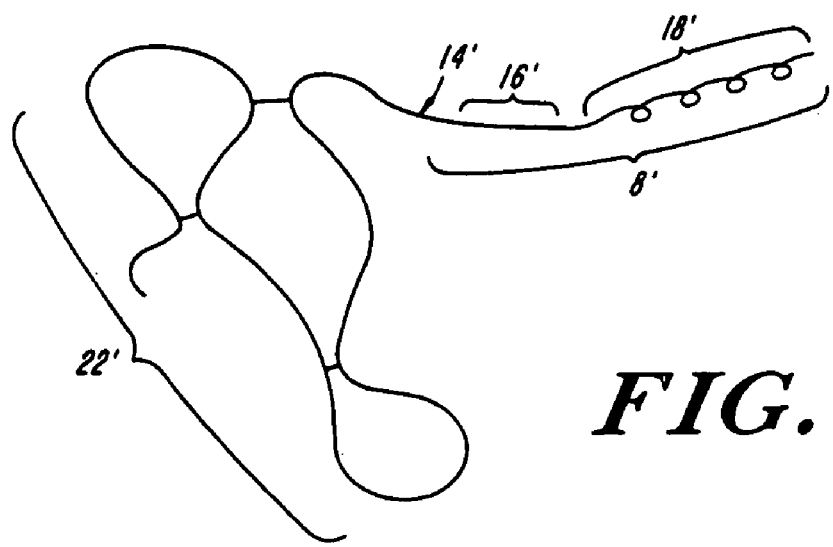
FIG. 2 is a schematic representation of the precursor fused polypeptide product of the invention comprising the hook with its cleavage site, hinge region, and leader polypeptide, fused to a target protein.
Figure 3:
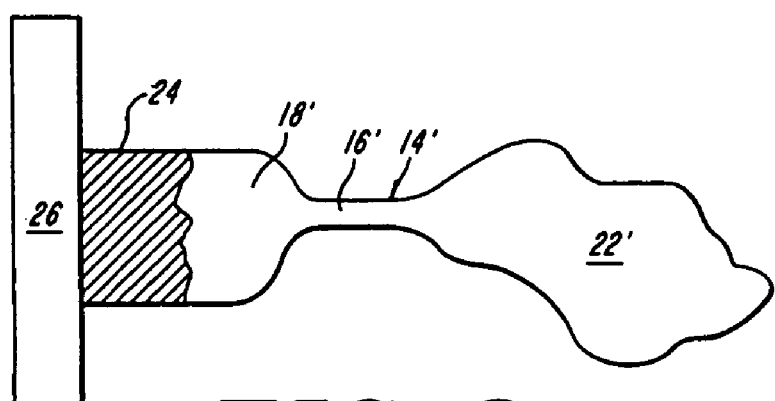
FIG. 3 is a schematic representation of the precursor fused polypeptide of FIG. 2 bound by means of a binding site engineered into its leader polypeptide to a receptor immobilized on a support matrix.

The fused DNA of the invention is illustrated in FIG. 1. The protein expressed by the DNA of FIG. 1 is illustrated in FIGS. 2 and 3, with polypeptide regions translated from the DNA regions identified by corresponding primed referenced characters. The DNA is composed of two distinct linked segments. The first segment encodes a polypeptide sequence most or all of which will ultimately be discarded. Linked to the DNA encoding the N or C terminus of the first segment is DNA encoding a target polypeptide—the protein of interest, which ultimately will be harvested. The first DNA segment is referred to herein as the "hook" or "hook region" 8. It contains nucleotides encoding three segments: a leader sequence 18, a sequence referred to herein as a "hinge" or "hinge region" 16, and an amino acid or amino acid sequence defining a cleavage site 14. The leader sequence may be a known sequence. Its primary function is to achieve high expressions of the fused polypeptide in accordance with the generally known fusion protein methodology of the prior art. The leader sequence 18 preferably also comprises a binding site designed to bind to a preselected receptor to facilitate purification, and/or a polypeptide structure designed to promote formation of inclusion bodies within the host cell or to have an affinity for charged or hydrophobic media. The cleavage site 14' is engineered into the protein by engineering the DNA. Its function is to serve as a site of action for a preselected cleavage agent. The function of the novel hinge region is to improve the rate and/or the specificity of the cleavage reaction. In the drawing the hook 8' is depicted as being attached to the N terminus of the target protein 22'. It can equally well be attached to the C terminus.

However, for clarity and convenience of description, the following discussion assumes the hook is a leader sequence at the N terminus.

Each of the regions defined above will now be discussed in detail.

The Hinge Region

As represented in FIGS. 1, 2 and 3, the hinge region 16' is encoded by a DNA segment 16. The hinge 16' is included in the fused protein to promote efficient cleavage at the cleavage site 14' by a selected cleavage agent. The expressed hinge region 16' is preferably an unstructured segment adjacent or about the cleavage site 14' comprising at least two amino acids that serve to expose the cleavage site to enzymatic or other digestion. This property of the hinge fosters accessibility of the cleavage site to enzymes or other cleavage reagents in the environment of the cleavage reaction and provides a kinetic advantage for preferential digestion at the amino acid residue(s) constituting the cleavage site. In short, the hinge facilitates the chemical or enzymatic reaction needed to excise the hook 8' from the cloned protein of interest 22'.

The amino acid sequence comprising the hinge region of the present invention can vary widely. It often comprises a flexible segment which imparts to the portion of the fused polypeptide about the cleavage site the ability to assume a relaxed random coil conformation. The amino acids comprising the hinge are responsible for imparting these properties. The combination of amino acids defining the hinge is therefore chosen for its ability to impart specific secondary properties to the portion of the polypeptide it comprises when the fused polypeptide is disposed in the cleavage environment.

Although each protein has an amino acid composition and sequence fixed during biosynthesis (primary structure), this sequence alone does not directly determine the protein's biological function or chemical properties. In the native state, each protein molecule has a characteristic three-dimensional shape or tertiary conformation determined and maintained by the combination of covalent, ionic, thermodynamic (hydrophobic), and other interactions of the individual amino acid residues. These are determined by the coaction of the properties of the individual amino acids in the amino acid sequence. It is thus the cumulative interacting properties of the amino acids in the sequence of the polypeptide chain which specify conformation in a particular solvent.

According to the invention, the hinge region comprises a sequence of amino acids which does not take a tertiary conformation which might sterically hinder access of the cleavage agent to its adjacent site of action. For this reason, the hinge region may contain at least one proline residue and be free of cysteine residues. Proline has a nonpolar aliphatic hydrocarbon side chain, and therefore is less soluble in water than amino acids having polar side groups. Proline differs from all other natural amino acids because it is actually a gamma-imino acid having its side chain attached to its alpha amino group.

The presence of one or more nonpolar proline residues substantially precludes the formation of alpha-helical structure in the hinge region. It promotes the formation in solution of an unstructured amino acid chain in the vicinity of the cleavage site, and thereby improves access of the cleavage agent to its site of action, improving the specificity of the cleavage reaction. The presence of proline in the hinge is preferred particularly if the leader peptide is one having a relatively fixed secondary structure such as an alpha helix or disulfide bonded conformation. Proline in this case serves to limit the possible steric interference to cleavage that may be occasioned by the presence of an adjacent leader having three dimensional structure.

Cysteine, on the other hand, contains a sulfhydryl or thiol group which is susceptible to oxidation resulting in a disulfide bond forming a covalent bridge between two cysteine residues. The presence of this highly reactive residue can work against the desired lack of fixed secondary structure of the hinge region, and therefore the use of cysteine is avoided in the hinge region.

The hinge region is a polypeptide chain containing from about two to twenty amino acids. In addition to being cysteine-free and typically containing at least one proline residue, the amino acid sequence of the hinge may exploit other design strategies which promote efficient cleavage in the preselected cleavage environment. It is known, for example, that many cleavage agents have both primary and secondary amino acid target sites. Accordingly, it can be advantageous in specific cases to include in the hinge one or more amino acids or amino acid sequences which constitute secondary sites of action for the preselected cleavage agent. This can have the effect of further increasing the affinity and accessibility of the cleavage agent for the cleavage site and can promote more efficient preferential cleavage at the appropriate cleavage site. The most specific site, however, must be adjacent the target polypeptide with less specific sites further away.

Particularly when the preselected cleavage agent is an endopeptidase, it is important that the hinge region be soluble in aqueous environments. Amino acids having charged side groups and hydrophilic properties are included in the hinge to promote solubility. These include the anionic residues Glu and Asp, the cationic residues Arg and Lys, and the neutral hydrophilic residues Ser and Thr.

The hinge region of the present invention is believed to function similarly to connecting regions found in immunoglobulin molecules. Immunoglobulins possess a flexible stretch of amino acids located between the CH-1 and CH-2 domains. Human IgG1, for example, contains in this region a sequence of 13 amino acid residues rich in prolines which account for the ability of an immunoglobulin molecule to assume a flexible Y-shape. Sites in or about this natural immunoglobulin hinge are readily cleaved by proteases, resulting in cleavage of the immunoblobulin into its now well characterized fragments.

One can design the hinge region in accordance with the foregoing principles by selection of appropriate codons in the DNA inserted between the leader sequence and the gene encoding the target polypeptide. Cleavage of the expressed fused protein at the built-in cleavage site in the vicinity of the hinge will be increased relative to cleavage of otherwise identical polypeptides which have no hinge. One can further improve and optimize reactivity of the cleavage site by additional empirically directed alterations to the amino acid sequence of the hinge region. Results from computer graphics/molecular dynamics calculations in conjunction with experimental observation of enzyme kinetics using various hinge sequences can often aid in this optimization by suggesting appropriate alterations to the prototype design of the hinge region.

To evaluate the efficacy of the hinge region in a given fused polypeptide, one constructs a "control DNA" coding for a fused polypeptide identical to the polypeptide to be evaluated, except that the codons encoding the hinge sequence have been deleted, such that the "control DNA" consists of codons that encode the leader sequence linked directly to the DNA which encodes the cleavage site which in turn is linked to the gene. The improvement in cleavage efficiency can be observed by treating the sample and control polypeptide encoded by the DNAs to the preselected cleavage agent. The reactions are conducted in the preselected conditions under which the sample polypeptide is to be cleaved. It will be found that the fused polypeptide including the hinge will be cleaved at the desired cleavage site preferentially to other potential cleavage sites, if any, in the polypeptide's structure, or will be cleaved at a faster rate. The sample fused polypeptide when treated typically yields greater amounts of the target polypeptide than does the control fused polypeptide.

Cleavage Site

The target protein 22' is preferably released from the remaining fusion material (the hook) 8' in an active form or one which readily reassumes its native conformation. Therefore, a portion of the hook 81 must encode a cleavage site 14' providing a site of action for the selected cleavage agent. Cleavage agents typically perform their function by hydrolysis of peptide bonds. The specificity of cleavage agents is determined by the identity of the amino acids at or near the peptide bond which is hydrolyzed. A given cleavage agent may recognize the bond between two specific amino acids, a bond following one or a specific sequence of amino acids, or a bond preceding a specific residue or sequence of amino acids.

The specificity of many cleavage agents is known. For example, trypsin cleaves preferentially at the carboxyl side of an arginine or lysine residue. Cyanogen bromide cleaves at methionine residues only under certain conditions, whereas pepsin with its broad specificity cleaves at the carboxyl side of most amino acid residues, preferably tyrosine, tryptophan, leucine, methionine, and phenylalanine. V-8 protease, cleaves only at glutamic acid or aspartic acid residues. Dilute acid cleaves between Asp-Pro. The table set forth below lists various known cleavage agents and their primary (and in some cases secondary) sites of action.

TABLE 1

Cleavage Agent - Cleavage Site Pairings

| Cleavage Agent of Action | Major Site of Action | Other Sites |
|---|---|---|
| Trypsin | Arg, Lys | |
| Chymotrypsin | Trp, Phe, Tyr | Leu, Met, His |
| Elastase | Neutral Aliphatic Residues | |
| Pepsin | Phe, Leu, Trp, | Ala, Gly, Glu |
| Papain | Arg, Lys, Gly | Wide specificity |
| Subtilisin | Aromatic and Aliphatic residues | Various |
| Thermolysin | Amino-linked bonds of Aliphatic residues | Ala, Phe |
| V-8 protease | Glu | Asp |
| Endoproteinase Arg C (Submaxillaris protease) | Arg | |
| Clostripain | Arg | |
| Thrombin | Arg | |
| Collagenase | X-Gly-Pro | X-Ala-Pro X-Gly-Thr |
| Lysobacter enzymogenes (endoproteinase Lys-C) | Lys | |
| Mysobacter A1-1 Protease | Lys | |

TABLE 1-continued

Cleavage Agent - Cleavage Site Pairings

| Cleavage Agent of Action | Major Site of Action | Other Sites |
|---|---|---|
| Armillaria mellea | Lys | |
| Flavobacterium meringosepticum | Pro | |
| Factor Xa | Ile-Glu-Gly-Arg (Sequence 1) | |
| CNBr | Met | |
| BNPS-skatole | Trp | |
| N-bromosuccinimide | Trp | |
| O-iodosobenzoic acid | Trp | |
| HBr/DMSO | Trp | |
| NTCB | Cys | |
| Sodium metal in liquid ammonia | Pro | |
| Hydroxylamine | Asn-Gly | |
| Dilute acid | Asp-Pro | |

Other cleavage agents are known. Those preferred for use in the inventions are enzymes with a primary site of action which cleave on the C-terminal side of the cleavage site residue (for hooks attached to the amino side of the target polypeptide) or on the N-terminal side of the cleavage site residue (for hooks attached to the carboxyl side of the target polypeptide). The currently most preferred cleavage agent/cleavage site pairing is V-8 protease/Glu.

The cleavage site in the fused protein of the invention generally can comprise any one or sequence of amino acids which can be cleaved by reactions specific to the site in an appropriate environment. Specificity of cleavage can be increased, and likelihood of undesired cleavage within the target peptide or elsewhere in the fused polypeptide can be decreased, by selection of a cleavage agent having a site of action which is absent from the target polypeptide. If, as is typical, the cleavage site is defined by only one or two amino acids, it is likely that the same amino acid or sequence is present in the target polypeptide. In such cases, the presence of the hinge gives a kinetic advantage to reaction at the site in the hook. Particularly if the hook is cysteine-free, or the leader sequence contains Cys residues disposed such that all will form intraleader disulfide bonds, the fused polypeptide may be cleaved after renaturation so that the target protein assumes its tertiary structure. This has the effect of masking potential cleavage sites in the target polypeptide. Being cysteine-free or having paired Cys residues, the hook remains free of disulfide bonds to extraneous contaminants, and its cleavage site, aided by the hinge, remains open to attack by the cleavage agent.

Alternatively, cleavage of the target polypeptide may be eliminated by altering its amino acid sequence to replace residues in its structure which may be subject to cleavage with chemically similar residues which, under the conditions of the cleavage reaction, are not cleaved. The currently preferred implementation of this strategy involves the use of Glu as a cleavage site and V-8 protease as the cleavage agent. Some fraction of the Glu residues present in the target protein are replaced by Asp residues. This may be accomplished readily by employing a variety of techniques known to those skilled in the art. For example, one can exploit a synthetic oligonucleotide corresponding to a section of the DNA of the target protein, except that the GAA or GAG codons for Glu are replaced by GAT or GAC codons for Asp. The DNA of the native protein is then restricted, and the spliced out section is replaced with the oligonucleotide. Because of the structural similarity of Glu and Asp, the resulting expressed analog can have bioproperties very similar to the native form of the protein.

The cleavage reaction is then conducted under conditions in which the V-8 protease cleaves at a Glu residue and does not cleave, or cleaves at a slower rate, at an Asp residue. For example, alkaline media, e.g., pH about 8.0, and the presence of acetate or carbonate, promotes Glu cleavage, and minimizes Asp cleavage.

When employing this amino acid replacement technique, it is often not necessary to replace all of the potential cleavage sites in the target protein, as in many cases they will be inaccessable to endoproteases because of the stereochemistry of renatured target protein.

As illustrated in the drawing, the cleavage site 14' is interposed between the hinge region 16' and the target polypeptide 22'. While this location is preferred, the cleavage site in some other embodiments may lie within the hinge region, that is, amino acid residues serving the function of the hinge may be interposed between the target polypeptide 22' and the cleavage site 14' (not illustrated). It is also within the concept of the invention for the cleavage site to be located in terminal regions of the amino acid sequence of a target polypeptide, and for the hinge region to be disposed immediately adjacent the natural polypeptide's amino acid sequence. In this case, cleavage results in a truncated analog of the native polypeptide, and the analog becomes the target polypeptide as that phrase is used herein. However, if a signal peptidase (in which the cleavage site is downstream from its site of specificity) were used as a cleavage enzyme, a native polypeptide could result.

Leader Sequence

A segment of DNA 18 within the hook 8 encodes a sequence of amino acids 18' designated herein as a leader sequence. The primary role of leader sequence 18 is to promote high expression and inhibit intracellular degradation of expressed product. Preferably, it also imparts to the fused polypeptide characteristics useful in purification. This polypeptide moiety may be designed to have characteristics that simplify the separation of the fused product from other materials. The amino acid sequence of the leader 18' can define a molecule having, for example, particular solubility characteristics, to facilitate separation of the fusion product from other polypeptides produced by the cellular host.

One preferred leader sequence defines an amphiphilic alpha-helical structure which contains both hydrophilic and hydrophobic amino acid residues, and can have an affinity for both polar and nonpolar media, depending on ambient solution conditions. The use of this type of leader promotes formation of insoluble inclusion bodies in host cells which aid in isolation of the product.

The currently preferred amino acid sequence for the amphiphilic helix leader and a DNA sequence which encodes it are set forth below:

```
ALA LYS ASN LEU ASN GLU ALA    (Sequences 2 & 3)

GCT AAA AAC CTT AAC GAA GCT
```

Repeats of 3–20 segments of the underlined amino acid sequence form aggregates within the producing cell to form inclusion bodies. Currently the tetramer of the helix is preferred, although additional modifications of the structure may have even more advantageous properties.

The amphiphilic helix is designed such that in its helical conformation one side presents a hydrophobic surface, comprising, for example, Phe, Ile, Val, Met, and/or Leu, Ala, or Trp residues, and the opposite side presents a hydrophilic surface, comprising Lys, Glu, and/or Asp residues. The amino acids which connect the sides are polar, uncharged helix formers, i.e., Asn or preferably Gln. His may be used in place of any of the foregoing residues.

When used as a leader, these structures promote formation of inclusion bodies in the cytoplasm of the producing cell. These can be dissolved in an appropriate aqueous denaturing solvent, and then precipitated as aggregates by altering the pH or ionic strength of the solvent. In high ionic strength media, the hydrophobic regions of the helix aggregate. Thus, the intracellular inclusion bodies may be collected, dissolved, and then purified by repeated changes in ionic strength or pH of the solvent. Further particulars of the amphiphilic helix leader are disclosed in copending application Ser. No. 07/028,500 filed together with this disclosure. The teaching of this application is incorporated herein by reference.

The leader may comprise a binding site, i.e., a DNA segment coding for amino acids defining a moiety useful in known isolation and purification techniques. In FIG. 3, the amino acid sequence defines a protein designated as 18' which selectively binds to a given receptor 24 immobilized on a support matrix 26. When the fused polypeptide having such a binding site is exposed to a support matrix, biospecific moiety 24 on the matrix 26 acts as a ligand which through biospecific recognition associates with the binding site to separate the fused product from impurities. Non-adsorbed material is removed by washing. The selected cleavage agent is then passed through the support matrix and reacts with the fused precursor product preferentially at the cleavage site exposed by the hinge region, thereby releasing the target protein and leaving the remainder of the fused material bound to the matrix.

Many binding site/receptor pairs are known in the art and have been exploited in various purification and isolation techniques including affinity chromatography and ion-exchange chromatography. For instance, polyanionic and polycationic segments bind to ion-exchangers, while Protein A binds to immunoglobulins immobilized on a matrix. Protein A, B-galactosidase, and chloramphenicol acetyltransferase have been used as binding regions in fusion methodology for the purpose of purification using affinity chromatography, and may be used in the process of this invention. DNA encoding a single chain, composite Fv of immunoglobulin may be used as a leader, with subsequent purification of the protein based on the Fv specificity for an immobilized antigen.

Target Proteins

The invention is essentially unlimited with respect to the identity of the target protein to be manufactured using the procedures and constructs disclosed herein. Indeed, an important feature of the invention is that it provides a generalized procedure which can be adapted readily to facilitate recombinant production of any desired protein. Thus, this invention may be used to produce growth factors, hormones, lymphokines, enzymes, antibodies or their various fragments including binding sites, viral and procaryotic proteins including both enzymatically active and inactive proteins, short polypeptides and various analogs of all of the above. Non-limiting examples include EGF, IGF-1, TGF alpha and beta, human collagenase inhibitor, PDGF, CTAP, Interleukins, interferons, industrial enzymes, thrombolytic agents, viral envelope proteins, bacterial membrane proteins, protein A and its fragments, and various synthetic peptides.

Cleavage Reaction

The purpose of including the hinge in the structure of the fused protein is to facilitate cleavage by a preselected cleavage agent in a preselected, typically aqueous environment. The pH, ionic environment, temperature, etc. of the cleavage reaction will depend on the particular cleavage agent/cleavage site involved. Suitable cleavage conditions are disclosed in the literature and are familiar to those skilled in the art.

The cleavage is preferably conducted under conditions in which the target polypeptide is folded in its tertiary conformation. If the target peptide contains two or more cysteine residues it may be stabilized in its native conformation by intramolecular disulfide bonds. Where cysteine is present in the leader, there is a possibility that it can form a disulfide bond with another residue, e.g., in the target polypeptide, resulting in a decrease in the rate of cleavage at site 14', or production of contaminating proteins, thereby complicating purification. Accordingly, the leader is often designed to be cysteine-free. If the leader contains two or more cysteines, renaturation of the fused polypeptide may also result in the formation of disulfide linkages in the leader. Because of the presence of the hinge, the renatured, three dimensional fused product will then comprise opposed leader and target polypeptides held in their three dimensional conformation, linked together by a hinge segment which permits and indeed facilitates digestion by the selected cleavage agent at the adjacent cleavage site.

This strategy may not be successful in confining cleavage to the cleavage site 14' if a potential cleavage site happens to be present in the amino acid sequence of the target polypeptide. However, because of the design of the hook as disclosed above, the cleavage reaction rate at a site within the target polypeptide will be less than the rate at site 14'. In such circumstances, particularly when a protease is used for cleavage, if the reaction is allowed to go to completion, both sites will be cleaved, with the result that little or no intact target polypeptide remains to be harvested.

In this case, in accordance with the invention, the cleavage reaction may be terminated before completion, the target polypeptide removed from the reaction mixture, and the remainder of the fused polypeptide again subjected to cleavage or, in effect, recycled. This strategy can reduce loss of target polypeptide by removing it from the reaction before the protease attacks the second, less reactive cleavage site. Further particulars of this cleavage technique are disclosed in copending application Ser. No. 07/746,281, filed on even date herewith, the disclosure of which is incorporated herein by reference.

It should be emphasized that the design of the hook is tailored to the preselected cleavage agent that will be used for releasing the target polypeptide in the environment in which the cleavage reaction is conducted. Thus, for example, a target polypeptide rich in Glu residues would not be produced with a hook containing a Glu cleavage site cleaved by V-8 protease; and a product having numerous Asp-Pro junctions would not be fused with a hook designed to exploit dilute acid cleavage. The cleavage environment often can be a very important success factor, as the stereochemistry of the fused polypeptide can be influenced by the presence of electrolytes and changes in pH.

The following examples more fully illustrate preferred features of the invention.

EXAMPLE 1

A series of fusion polypeptides comprising epidermal growth factor (EGF) linked to hook polypeptides of various designs were expressed in prokaryotes by transfecting *E. coli* with expression vectors made by inserting DNA encoding the various fused polypeptide products in the BglII, EcoRI, and BamHI sites of plasmid pKK (Amman et al—Pharmacia) modified to promote high copy number and to impart tetracycline resistance; and plasmid pGG, derived from pBr322, and modified to contain the trp promoter. Each of the transformants were cultured and about 50 milligrams fusion product per gram of wet cell paste were collected. Three different hook regions were designed, all of which comprised a glutamic acid residue immediately adjacent the asparagine residue constituting the amino terminal of the EGF target protein. Polypeptide 1 had a truncated TRP-LE sequence as a leader connected at its carboxyl end, via the glutamic acid residue, to the EGF. It thus contained no engineered hinge region. Polypeptide 2 was designed to have in sequence an arginine, aspartic acid, and leucine residue disposed between the truncated TRP-LE and the glutamic acid cleavage site. It was hypothesized that this tripeptide could be useful as a hinge because Asp and Arg are charged residues and therefore might promote relaxation of the section of the fused polypeptide adjacent the cleavage site by increasing its solubility. Peptide 3 included a hook comprising in sequence the truncated TRP-LE followed by 43 residues derived from the TRP leader sequence (which had been modified by conventional techniques to change the native Met residues to Val and the Glu residues to Asp) Asp-Leu as a hinge, the Glu cleavage site, and the EGF. The amino acid structure of each of these hook regions are set forth below.

P-1

MET-LYS-ALA-ILE-PHE-VAL-LEU-LYS-GLY-SER-LEU-ASP-<u>GLU</u>-EGF  (Sequence 4)

P-2

MET-LYS-ALA-ILE-PHE-VAL-LEU-LYS-GLY-SER-LEU-ASP-<span style="text-decoration:overline">ARG</span>-  (Sequence 5)

<span style="text-decoration:overline">ASP-LEU</span>-<u>GLU</u>-EGF

P-3

MET-LYS-ALA-ILE-PHE-VAL-LEU-LYS-GLY-SER-LEU-ASP-  (Sequence 6)

ARG-ASP-LEU-ASP-SER-ARG-LEU-ASP-LEU-ASP-VAL-

ARG-THR-ASP-HIS-LYS-ASP-LEU-SER-ASP-HIS-LEU-

VAL-LEU-VAL-ASP-LEU-ALA-ARG-ASN-ASP-LEU-ALA-

ARG-ILE-VAL-THR-PRO-GLY-SER-ARG-TYR-VAL-

ALA-A̅S̅P̅-L̅E̅U̅-GLU-EGF

The overlined residues constitute the hinge; the underlined residues constitute the cleavage site; EGF indicates the known amino acid sequence of human epidermal growth factor; and the remaining residues constitute the leaders.

The 53 amino acid EGF protein contains Glu residues at positions 5, 24, 40, and 51. Previous experiments had indicated that the Glu residues at positions 5, 24, and 40 were not significantly cleaved by V-8 protease when the EGF had been renatured and was held in its native conformation by three disulfide bonds spanning cysteine residues 6–20, 14–31, and 33–42. The Glu residue at position 51, however, was cleaved rather efficiently, resulting in a 51 amino acid EGF analog. The purpose of the design of the foregoing leaders was to produce a fused protein which could be cleaved preferentially at the Glu cleavage site by V-8 protease.

Figure 5:
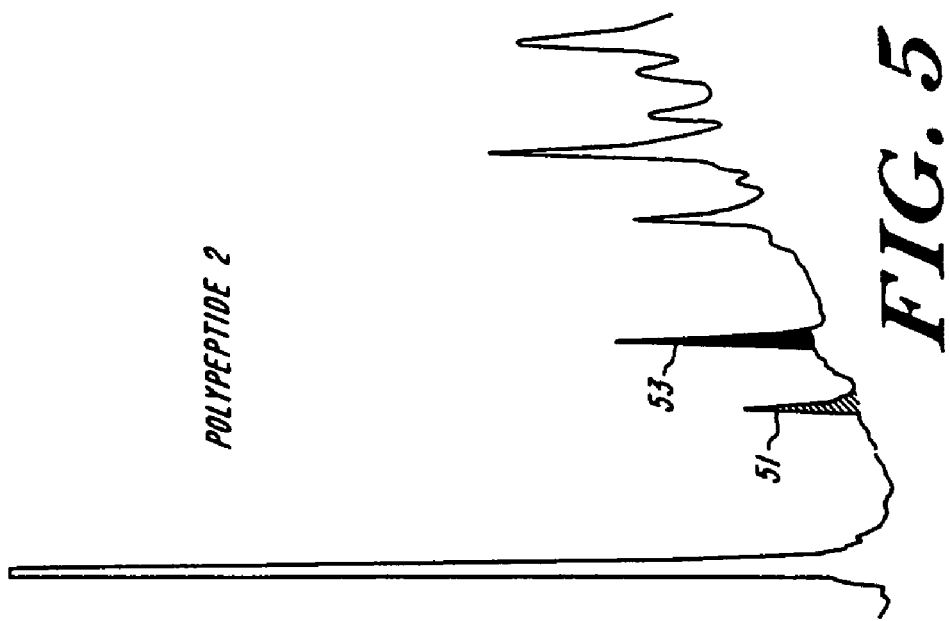
Figure 4:
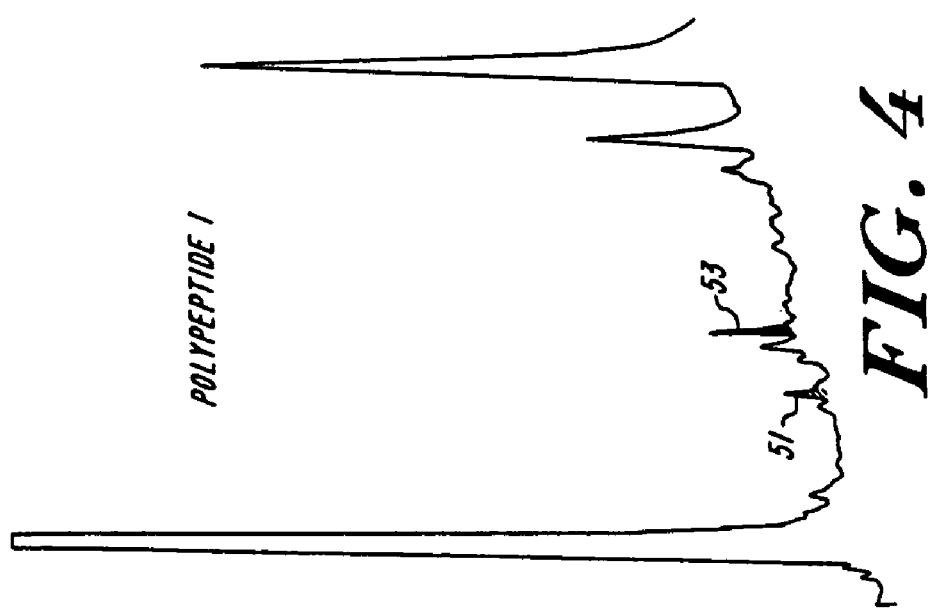

Each of the fused polypeptide products was subjected to V-8 protease for one hour. V-8 protease (ICN) was added at a concentration of 1% of the fused polypeptide concentration, which was set at about 1.0 mg/ml. The cleavage was conducted at 37° C. in 100 mM ammonium acetate and 1 mM EDTA, pH 8. Prior to the addition of the enzyme, the fused proteins were renatured by dissolving collected inclusion bodies in urea. After approximately 12–16 hours at room temperature, the urea was dialyzed out. If renaturation is omitted, treatment with V-8 protease cleaves at all four Glu residues in the EGF structure. The cleavage reactions were stopped by decreasing the temperature to 4° C. and dilution with 20 mM phosphate buffer, pH7. 50 microliter samples of the reaction mixtures were injected into a C-18 HPLC column (5 micron) previously equilibrated with the buffer (82% sodium phosphate, 18% acetonitrile) to resolve the components. Elution was conducted with an 18% to 32% acetonitrile gradient. Protein was detected by absorbance at 214 nm. After 5–10 minutes the cleaved 51 amino acid and 53 amino acid EGFs were detected. The chromatograms for the three samples are shown in FIGS. 4, 5, and 6. Polypeptide 1 was cleaved at a much slower rate than was polypeptide 2 or 3. After 1 hour, more 53 than 51 was produced in all three samples, but cleavage efficiency was increased in the polypeptides containing the hinge regions (2 and 3), and selectivity of cleavage was improved in polypeptide 3.

It was noted particularly with respect to polypeptide 3, that the ratio of the 53 amino acid EGF to the 51 amino acid analog decreased as the total amount of fused polypeptide cleaved increased. When 10% of the protein was cleaved, the 53/51 ratio was approximately 3:1, whereas when 50% of the protein was cleaved, the ratio was about 1:3. Accordingly, the cleavage was optimized by empirically determining the time point when the maximum 53:51 ratio was observed, and the reaction was stopped at that time by lowering the temperature and adding HCl to lower the pH to 5.5. At this pH, most of the fused polypeptide remaining precipitates, whereas the 53 and 51 amino acid EGFs remain dissolved, thereby permitting separation. The fused product was then resubjected to the V-8 protease protedytic cleavage agent, and the cleavage reaction was repeated. The results of this recycle method are set forth below.

| Cycle EGF | Protein in Supernatant (mg) | 53 EGF (ug) | 51 EGF (ug) |
|---|---|---|---|
| 1 | 0.27 | 51 | 16 |
| 2 | 0.19 | 38 | 30 |
| 3 | 0.17 | 36 | 34 |
|   |      | 125 | 80 |

It was discovered that in the presence of sodium dodecyl sulfate, sodium laurate, or 2% N-dodecyl, N-3-propane sulfonic acid, N,N-dimethyl ammonium (Zwitterion 3–12), cleavage to produce 53 amino acid EGF over 51 amino acid EGF was favored further. For example, in the presence of 2% SDS, after 3 hours of reaction, the ratio of the 53 to 51 EGF is greater than 20:1 (see HPLC plot, FIG. 7).

EXAMPLE II

A series of fused polypeptides were prepared by engineering DNAs which were subsequently transfected into *E coli* and expressed. All of the inserted DNA constructs comprised a leader sequence encoding beta galactosidase, connected through a hinge and one or more cleavage sites disposed within or adjacent the hinge, to human calcitonin. The structure of the fused polypeptides are set forth below:

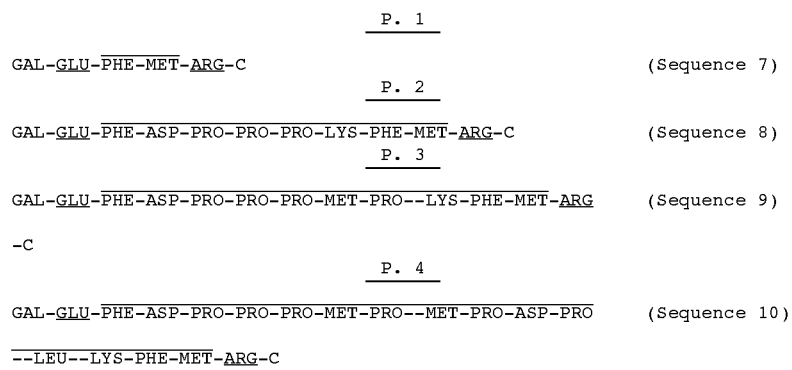

P. 1

GAL-GLU-P̅H̅E̅-M̅E̅T̅-ARG-C                                    (Sequence 7)

P. 2

GAL-GLU-P̅H̅E̅-A̅S̅P̅-P̅R̅O̅-P̅R̅O̅-P̅R̅O̅-L̅Y̅S̅-P̅H̅E̅-M̅E̅T̅-ARG-C          (Sequence 8)

P. 3

GAL-GLU-P̅H̅E̅-A̅S̅P̅-P̅R̅O̅-P̅R̅O̅-P̅R̅O̅-M̅E̅T̅-P̅R̅O̅--L̅Y̅S̅-P̅H̅E̅-M̅E̅T̅-ARG      (Sequence 9)

-C

P. 4

GAL-GLU-P̅H̅E̅-A̅S̅P̅-P̅R̅O̅-P̅R̅O̅-P̅R̅O̅-M̅E̅T̅-P̅R̅O̅--M̅E̅T̅-P̅R̅O̅-A̅S̅P̅-P̅R̅O̅   (Sequence 10)

--L̅E̅U̅--L̅Y̅S̅-P̅H̅E̅-M̅E̅T̅-ARG-C

GAL refers to the known sequence of beta galactosidase, C refers to the known sequence of human calcitonin (molecular weight approximately 3500 d), the overlined residues constitute the hinge, the underlined residues constitute potential cleavage sites. These constructs were designed to be cleaved either by endopeptidase Arg-C or V-8 protease, having sites of action on the C-terminal side of Arg and Glu residues, respectively.

The hinge of fused polypeptide 1 (p.1) was designed in an attempt to promote cleavage by endo-Arg-C protease at the Arg residue immediately adjacent the first amino acid of calcitonin. Polypeptides 2, 3, and 4 (p2, p3, p4) contained progressively longer hinge regions rich in proline, which should result in randomly coiled polypeptide segments adjacent or about the potentially cleavable Arg residues and the Glu residue.

The expressed fusion polypeptides were purified by differential solubilization and DEAE-cellulose chromatography. The low solubility of the fusion proteins permitted a relatively simple purification procedure. Differential solubilization is initially used to extract proteins that are soluble in aqueous buffer and in, 1% detergent (Triton X-100). At this stage, the fusion proteins are solubilized in 6 M urea and are approximately 70% pure. The protein is then applied to a DEAE-cellulose column equilibrated with 6 M urea, and eluted with a linear gradient of NaCl. Following chromatography, the fusions are approximately 90% pure. The yield of purified fusion is 20 mg/g of cell paste.

The purified fusions were cleaved with V-8 protease or endo-Arg C protease. Different reaction conditions were used for each protease. For V-8 protease protease reactions, the fusions were dialyzed versus 2 M urea, 87 mM ammonium acetate, 0.1 mM EDTA, pH 7.8, and digestions were carried out for 2 hrs. at 22° C. with an enzyme to substrate ratio of 1:50. For endo-Arg C protease reactions, the fusions were dialyzed versus 6 M urea, 20 mM Tris-HCl, 0.1 mM EDTA, pH 8, and digestions were carried out for 2 hrs. at 22° C. with an enzyme to substrate ratio of 1:15. The reactions in all cases were terminated by heating the samples after addition of 1% SDS and 20 mM dithiothreitol (DTT).

The cleavage products were separated, and the presence and relative quantity of calcitonin and calcitonin analogs were determined by Western blot analysis. In this assay, the cleavage products are separated by SDS gel electrophoresis and electrophoretically transferred to nitrocellulose paper. Calcitonin is then localized on the paper using anti-calcitonin antiserum.

Endo-Arg C protease cleavage produced no detectable quantities of intact calcitonin in any of the constructs. However, a major immunoreactive fragment was produced in polypeptide 1 and 2 digestions having a molecular weight of 10,000 daltons. No smaller immunoreactive species were found. Polypeptide 3 and 4 digestions did not show any 10,000 daltons or smaller immunoreactive fragments.

V-8 protease proteolytic cleavage, of course, did not produce free calcitonin, as cleavage at the GLU residue left the hinge attached to the N-terminus of the calcitonin. However, as the length of the hinge region increased, increasing amounts of stable, immunoreactive calcitonin analogs (hinge and calcitonin) were produced. The molecular weight of these fragments, which increased with the size of the hinge, was used along with immunoreactivity to identify each analog.

The V-8 protease protease and endo-Arg C cleavage results are set forth in the table below.

| Peptide | Cleavage Agent | Intact HC | Immunoreactive Polypeptides |
|---|---|---|---|
| p1 | V-8 protease | — | + |
|    | endo-Arg-C | 0 | + |
| p2 | V-8 protease | — | + |
|    | endo-Arg-C | 0 | + |
| p3 | V-8 protease | — | ++ |
|    | endo-Arg-C | 0 | 0 |
| p4 | V-8 protease | — | +++ |
|    | endo-Arg-C | 0 | 0 |

The identity of the calcitonin analog released from polypeptide 1 after V-8 protease cleavage has been confirmed by sequence analysis to be Phe-Met-Arg-calcitonin. The chromatogram from HPLC analysis of such a digest on a C-18 column developed with a acetonitrile/trifluoroacetic acid (0.1% TFA) gradient is complex since the fusion protein has a molecular weight of about 124,000 daltons (leader approximately 120,000 daltons, hinge calcitonin, approximately 3500 daltons) and contains numerous Glu residues. The calcitonin analog was shown by western blot analysis to correspond to a specific fraction in the HPLC separation. The fraction was then rechromatographed on a C-8 column yielding pure Phe-Met-Arg-calcitonin.

Isolated Phe-Met-Arg-calcitonin can be cleaved to yield free calcitonin using endo-Arg C protease. The calcitonin can then be isolated by C-18 column chromatography. Its identity has been confirmed by sequence analysis and tryptic peptide mapping.

EXAMPLE III

A series of fusion polypeptides comprising calcitonin and calcitonin analogs linked to hook polypeptides of various designs were expressed in *E. coli*. Each fusion protein had designed hook and hinge regions. Each hook contained a glutamic acid residue immediately preceding the N-terminal cysteine residue of calcitonin. The calcitonin was designed to be released from the fusion by cleavage at the Glu residue by V-8 protease.

Polypeptide I had a TRP-LE sequence (188 residues) as a leader, connected at its carboxyl end to a hinge (Phe-Pro-Gly) region, followed by the glutamic acid residue and human calcitonin. It was hypothesized that this hinge tripeptide would promote cleavage at the Glu residue by providing a flexible residue (proline) and an uncharged "spacer" residue next to the Glu residue. The large leader (27,000 daltons) was used to promote high expression levels. Small leader sequences such as a 17-residue truncated TRP-LE resulted in no expression.

Polypeptide 2 had a modified truncated TRP-LE sequence comprising in sequence a truncated TRP-LE (15 residues) followed by 43 residues derived from the TRP leader sequence (which had been modified by conventional techniques to change the native 3 Met residues to Val, the native 4 Glu residues to Asp, and the single Cys residue to Ser), Asp-Leu as the hinge, the Glu cleavage site, and a salmon calcitonin analog. The salmon calcitonin analog had an Asp at position 15 instead of the native Glu. The internal Glu was discovered to be easily cleaved by V-8 protease. Construction of a calcitonin analog sought to obviate this difficulty. A Gln 15 analog was initially constructed but the fusion expression level was very low. An Asp 15 analog constructed subsequently demonstrated high expression levels.

The structures of polypeptide 1 and 2 are set forth below, the underlined residues indicating desired cleavage sites, the overlined residues indicating the hinge, HC indicating human calcitonin, and SC the salmon calcitonin analog.

The purified fusions were subsequently dissolved in Tris/EDTA buffer containing 8 M urea, and passed through a DEAE-cellulose column equilibrated with 6 M urea. The fusion proteins passed through the column unretarded, but

```
                Polypeptide 1 (Sequence 11)

MET LYS ALA ILE PHE VAL LEU LYS GLY SER LEU ASP ARG

ASP LEU ASP SER ARG ILE GLU LEU GLU MET ARG THR ASP

HIS LYS GLU LEU SER GLU HIS LEU MET LEU VAL ASP LEU

ALA ARG ASN ASP LEU ALA ARG ILE CYS THR PRO GLY SER

ARG TYR VAL ALA ASP LEU THR LYS VAL ASP ARG TYR SER

TYR VAL MET HIS LEU VAL SER ARG VAL VAL GLY GLU LEU

ARG HIS ASP LEU ASP ALA LEU HIS ALA TYR ARG ALA CYS

MET ASN MET GLY THR LEU SER GLY ALA PRO LYS VAL ARG

ALA MET GLN LEU ILE ALA GLU ALA GLU GLY ARG ARG ARG

GLY SER TYR GLY GLY ALA VAL GLY TYR PHE THR ALA HIS

GLY ASP LEU ASP THR CYS ILE VAL ILE ARG SER ALA LEU

VAL GLU ASN GLY ILE ALA THR VAL GLN ALA GLY ALA GLY

VAL VAL LEU ASP SER VAL PRO GLN SER GLU ALA ASP GLU

THR ARG ASN LYS ALA ARG ALA VAL LEU ARG ALA ILE ALA

THR ALA HIS HIS ALA GLN GLU PHE PRO GLY GLU HC
                                   ‾‾‾ ‾‾‾ ‾‾‾

Polypeptide 2 (Sequence 12)

MET LYS ALA ILE PHE VAL LEU LYS GLY SER LEU

ASP ARG ASP LEU ASP SER ARG LEU ASP LEU ASP

VAL ARG THR ASP HIS LYS ASP LEU SER ASP HIS

LEU VAL LEU VAL ASP LEU ALA ARG ASN ASP LEU

ALA ARG ILE VAL THR PRO GLY SER ARG TYR VAL

ALA ASP LEU GLU SC
           ‾‾‾ ‾‾‾
```

Smaller hook sequences were also designed, but resulted in little or no expression of the fusion polypeptides. Polypeptide I demonstrated good expression levels (15–20%), but because of the presence of multiple Glu and Cys residues in the leader sequence, the post-digestion mixture was complex, containing many fragments, including disulfide linked combinations of fragments. Thus, it was desirable to design a fusion polypeptide that was as small as possible to achieve good expression and could be cleaved into only 2 fragments (the hook/hinge fragment and calcitonin) by V-8 protease. Polypeptide 2 was designed with that goal in mind. The hinge in polypeptide 2 was designed to facilitate cleavage with V-8 protease such that the cleavage reaction approached 100% completion.

Each of the fusion proteins was purified by differential solubilization and DEAE chromatography. Most contaminating proteins were removed from the insoluble fusion proteins by washes with detergent (Triton X-100) and low ionic strength buffers. All steps of the purification contained 10 mM EDTA to retard proteolytic digestions by E. coli proteases co-purifying with the fusion proteins.

some contaminating proteins and DNA were removed from the preparations through binding to the column material.

Each of the purified fusions was cleavable with V-8 protease. The fusions were diluted with the appropriate buffer such that the final protein concentration was 1.0 mg/ml and the buffer conditions were 4 M urea, 20 mM ammonium acetate, 1.0 mM EDTA, pH 7.8. Polypeptide 1 was cleaved with an enzyme to substrate ratio of 1:25 for 36 hrs. at 22° C. The human calcitonin was then purified from the resulting mixture of polypeptides by HPLC in water/acetonitrile (0.1% TFA) gradient. Polypeptide 2 was cleaved after first reducing the fusion with 1.5 mM DTT. An enzyme to substrate ratio of 1:500 was sufficient to achieve complete cleavage within 2 hrs. at 22° C. The resulting mixture contained only 2 polypeptides (the hook and calcitonin analog) which were easily separated by carboxymethyl cellulose chromatography. Polypeptide 1 cleavage was 25–50% complete at the Glu residue amino terminal to calcitonin, while polypeptide 2 cleavage was consistently obtained at greater than 95%. The structure of the released calcitonin molecules has been confirmed by sequence analysis.

EXAMPLE IV

A series of fusion polypeptides comprising fragment B (FB) of protein A linked to hook polypeptides of various designs were expressed in *E. coli*. Each fusion had designed hook and hinge regions. Each hook contained a methionine residue adjacent the hinge region such that the FB or FB analog could be released from the fusion by cleavage at the Met residue by cyanogen bromide (CNBr). All fusions were designed to contain only one Met residue.

One of the fused polypeptides had a truncated TRP-LE sequence as a leader connected at its carboxy-terminal end of FB via the Met residue and a hinge region separating the Met and a Cys residue on the N-terminus of FB. The Met-Cys sequence cannot be cleaved by CNBr, so a hinge was designed whereby a minimum number of residues could be inserted carboxy-terminal to the Met to promote cleavage. The sequence Pro—Pro satisfied this objective.

The structure of the polypeptides with and without the hinge are set forth below. FB indicates the known amino acid sequence of the FB fragment of protein A having a Cys residue on its N terminus, the underlined residues indicate the cleavage site; and the overlined residues indicate the hinge.

Polypeptide With Hinge (Sequence 13)

MET LYS ALA ILE PHE VAL LEU LYS GLY SER LEU

ASP ARG ASP LEU GLU PHE MET PRO PRO CYS FB

-continued

Polypeptide Without Hinge (Sequence 14)

MET LYS ALA ILE PHE VAL LEU LYS GLY SER LEU

ASP ARG ASP LEU GLU PHE MET CYS FB

Each of the fusion proteins was soluble upon lysing the *E. coli* with sonication in 50 mM Tris-HCl buffer, pH 8. The crude cell extracts contained approximately 20–30% fusion protein.

After dialysis versus $H_2O$ and freeze-drying, the protein was cleaved with CNBr (0.5 g CNBr per g cell paste) in 0.1 N HCl for 6 hrs. at 22° C. in the dark. Following freeze drying, the cleavage products were dissolved in 20 mM Tris-HCl, pH 8 and applied to a DEAE-cellulose column for partial purification of the FB and FB analogs. Final purification was accomplished using HPLC developed with an acetonitrile/TFA gradient. A large yield of the N-Cys analog of FB was obtained when the fusion polypeptide having the hinge was treated. No detectable yield was observed upon treatment of the hinge-free polypeptide. The identification of the released FB molecules has been confirmed by sequence analysis.

The invention may be embodied in other specific forms without departing from the spirit and scope thereof. Accordingly, other embodiments are within the following claims.

What is claimed is:

1. A fused polypeptide produced by an organism by expression of a recombinant DNA, said polypeptide comprising a combination of:

a first sequence of amino acids comprising a leader sequence, a hinge region, and at least one amino acid defining a cleavage site recognizable and cleavable by a selected enzymatic cleavage agent, said hinge region being a cysteine-free flexible amino acid sequence not normally associated with said leader sequence and comprising at least two amino acids defining a secondary structure which promote cleavage by said cleavage agent at said cleavage site, and a second sequence of amino acids linked to said first sequence defining a selected target polypeptide, whereby said cleavage site is a favored site for cleavage upon treatment of said fused polypeptide with said cleavage agent when said fused polypeptide is disposed in solution and said second amino acid sequence defining said selected target polypeptide is disposed in its three-dimensional conformation said second sequence of amino acids comprising an antigen-binding fragment of an antibody.

2. The fused polypeptide of claim 1 wherein said leader sequence is adapted to facilitate concentration of said fused polypeptide.

3. The fused polypeptide of claim 2 wherein said leader sequence comprises an amphiphilic helix.

4. The fused polypeptide of claim 1 wherein said hinge region comprises at least one proline residue.

5. The fused polypeptide of claim 1 wherein said hinge region comprises an amino acid sequence which forms a random coil when said fused polypeptide is disposed in aqueous solution.

6. The fused polypeptide of claim 1 wherein said hinge region includes a member selected form the group consisting of aspartic acid, glutamic acid, lysine, arginine, serine, threonine, proline, and combinations thereof in amounts sufficient to render said hinge region soluble in water.

7. The fused polypeptide of claim 1 wherein said hinge region comprises:

a flexible cysteine-free amino acid sequence not normally associated with said leader sequence or said selected target polypeptide.

8. The fused polypeptide of claim 1 wherein said cleavage site is rendered preferentially accessible to said cleavage agent by said hinge region, thereby promoting preferential cleavage of said target polypeptide from said first sequence at said cleavage site in an environment in which said target polypeptide is disposed in its three dimensional conformation.

9. The fused polypeptide of claim 1 wherein said cleavage site is immediately adjacent said second amino acid sequence.

10. The fused polypeptide of claim 1 wherein said cleavage site comprises one or a sequence of amino acids absent from the sequence comprising said target polypeptide.

11. The fused polypeptide of claim 1 wherein said cleavage side comprises a unique one or sequence of amino acids in said fused polypeptide.

12. The fused polypeptide of claim 1 wherein said cleavage site comprises a Glu residue.

13. The fused polypeptide of claim 12 wherein said cleavage site is cleaved by *S. aureus* V-8 protease.

14. A fused polypeptide produced by an organism by expression of a recombinant DNA, said fused polypeptide encoded by a recombinant DNA comprising a combination of:

a first DNA segment encoding a sequence of amino acids comprising a leader sequence, a hinge region, and at least one amino acid defining a cleavage site recognizable and cleavable by a selected enzymatic agent, said hinge region being a cysteine-free flexible amino acid sequence not normally associated with said leader sequence and comprising at least two amino acids defining a secondary structure which can promote cleavage by said cleavage agent at said cleavage site; and a second DNA segment linked to said first segment encoding a sequence of amino acids defining a selected target polypeptide, whereby said cleavage site is a favored site for cleavage upon treatment of said fused polypeptide with said cleavage agent when said fused polypeptide is disposed in solution and said amino acid sequence defining a target polypeptide is disposed in its three dimensional conformation said second sequence of amino acids comprising an antigen-binding fragment of an antibody.

15. The fused polypeptide of claim 14 wherein the recombinant DNA encoding said first DNA segment comprises DNA encoding a leader sequence comprising an amino acid sequence which imparts a preselected property to said fused polypeptide operable to facilitate concentration of said fused polypeptide.

16. The fused polypeptide of claim 14 wherein the recombinant DNA encoding said cleavage site comprises DNA encoding one or a sequence of amino acids absent from said sequence defining said target polypeptide.

17. The fused polypeptide of claim 14 wherein the recombinant DNA encoding said hinge region comprises DNA encoding a flexible cysteine-free amino acid sequence not normally associated with said leader sequence or said selected target polypeptide.

18. The fused polypeptide of claim 14 in which at least one of the two amino acids is proline.

* * * * *

SEQUENCE LISTING

```
(1) GENERAL INFORMATION:

(iii) NUMBER OF SEQUENCES: 14

(2) INFORMATION FOR SEQ ID NO:1:

(i) SEQUENCE CHARACTERISTICS:
          (A) LENGTH: 4 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:1:

Ile Glu Gly Arg
1

(2) INFORMATION FOR SEQ ID NO:2:

(i) SEQUENCE CHARACTERISTICS:
          (A) LENGTH: 21 base pairs
          (B) TYPE: nucleic acid
          (C) STRANDEDNESS: double
          (D) TOPOLOGY: linear (ii) MOLECULE TYPE: cDNA
```

(iii) HYPOTHETICAL: NO (iv) ANTI-SENSE: NO (v) FRAGMENT TYPE: N-terminal (ix) FEATURE:
             (A) NAME/KEY: CDS
             (B) LOCATION: 1..21

(xi) SEQUENCE DESCRIPTION: SEQ ID NO:2:

```
GCT AAA AAC CTT AAC GAA GCT                                    21
Ala Lys Asn Leu Asn Glu Ala
 1               5
```

(2) INFORMATION FOR SEQ ID NO:3:

(i) SEQUENCE CHARACTERISTICS:
             (A) LENGTH: 7 amino acids
             (B) TYPE: amino acid
             (D) TOPOLOGY: linear (ii) MOLECULE TYPE: protein (xi) SEQUENCE DESCRIPTION: SEQ ID NO:3:

```
Ala Lys Asn Leu Asn Glu Ala
 1               5
```

(2) INFORMATION FOR SEQ ID NO:4:

(i) SEQUENCE CHARACTERISTICS:
             (A) LENGTH: 13 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:4:

```
Met Lys Ala Ile Phe Val Leu Lys Gly Ser Leu Asp Glu
 1               5                  10
```

(2) INFORMATION FOR SEQ ID NO:5:

(i) SEQUENCE CHARACTERISTICS:
             (A) LENGTH: 16 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:5:

```
Met Lys Ala Ile Phe Val Leu Lys Gly Ser Leu Asp Arg Asp Leu Glu
 1               5                  10                  15
```

(2) INFORMATION FOR SEQ ID NO:6:

(i) SEQUENCE CHARACTERISTICS:
            (A) LENGTH: 59 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:6:

Met Lys Ala Ile Phe Val Leu Lys Gly Ser Leu Asp Arg Asp Leu Asp
 1               5                  10                  15

Ser Arg Leu Asp Leu Asp Val Arg Thr Asp His Lys Asp Leu Ser Asp
            20                  25                  30

His Leu Val Leu Val Asp Leu Ala Arg Asn Asp Leu Ala Arg Ile Val
        35                  40                  45

Thr Pro Gly Ser Arg Tyr Val Ala Asp Leu Glu
    50                  55

(2) INFORMATION FOR SEQ ID NO:7:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:7:

Glu Phe Met Arg
 1

(2) INFORMATION FOR SEQ ID NO:8:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:8:

Glu Phe Asp Pro Pro Pro Lys Phe Met Arg
 1               5                  10

(2) INFORMATION FOR SEQ ID NO:9:

(i) SEQUENCE CHARACTERISTICS:
            (A) LENGTH: 13 amino acids
            (B) TYPE: amino acid
            (C) STRANDEDNESS: single (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:9:

Glu Phe Asp Pro Pro Pro Met Pro Arg Lys Phe Met Arg
1               5                   10

(2) INFORMATION FOR SEQ ID NO:10:

(i) SEQUENCE CHARACTERISTICS:
         (A) LENGTH: 20 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:10:

Glu Phe Asp Pro Pro Pro Met Pro Arg Met Pro Asp Pro Glu Leu Arg
1               5                   10                  15

Lys Phe Met Arg
            20

(2) INFORMATION FOR SEQ ID NO:11:

(i) SEQUENCE CHARACTERISTICS:
         (A) LENGTH: 193 amino acids
         (B) TYPE: amino acid
         (C) STRANDEDNESS: single
         (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:11:

Met Lys Ala Ile Phe Val Leu Lys Gly Ser Leu Asp Arg Asp Leu Asp
1               5                   10                  15

Ser Arg Ile Glu Leu Glu Met Arg Thr Asp His Lys Glu Leu Ser Glu
                20                  25                  30

His Leu Met Leu Val Asp Leu Ala Arg Asn Asp Leu Ala Arg Ile Cys
            35                  40                  45

Thr Pro Gly Ser Arg Tyr Val Ala Asp Leu Thr Lys Val Asp Arg Tyr
        50                  55                  60

Ser Tyr Val Met His Leu Val Ser Arg Val Gly Glu Leu Arg His
65                  70                  75                  80

Asp Leu Asp Ala Leu His Ala Tyr Arg Ala Cys Met Asn Met Gly Thr
                85                  90                  95

Leu Ser Gly Ala Pro Lys Val Arg Ala Met Gln Leu Ile Ala Glu Ala
            100                 105                 110

```
Glu Gly Arg Arg Arg Gly Ser Tyr Gly Gly Ala Val Gly Tyr Phe Thr
            115                 120                 125
Ala His Gly Asp Leu Asp Thr Cys Ile Val Ile Arg Ser Ala Leu Val
            130                 135                 140
Glu Asn Gly Ile Ala Thr Val Gln Ala Gly Ala Gly Val Val Leu Asp
145                 150                 155                 160
Ser Val Pro Gln Ser Glu Ala Asp Glu Thr Arg Asn Lys Ala Arg Ala
                165                 170                 175
Val Leu Arg Ala Ile Ala Thr Ala His His Ala Gln Glu Phe Pro Gly
            180                 185                 190
Glu
```

(2) INFORMATION FOR SEQ ID NO:12:

(i) SEQUENCE CHARACTERISTICS:
        (A) LENGTH: 59 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:12:

```
Met Lys Ala Ile Phe Val Leu Lys Gly Ser Leu Asp Arg Asp Leu Asp
1               5                   10                  15
Ser Arg Leu Asp Leu Asp Val Arg Thr Asp His Lys Asp Leu Ser Asp
            20                  25                  30
His Leu Val Leu Val Asp Leu Ala Arg Asn Asp Leu Ala Arg Ile Val
            35                  40                  45
Thr Pro Gly Ser Arg Tyr Val Ala Asp Leu Glu
    50                  55
```

(2) INFORMATION FOR SEQ ID NO:13:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:13:

```
Met Lys Ala Ile Phe Val Leu Lys Gly Ser Leu Asp Arg Asp Leu Glu
1               5                   10                  15
Phe Met Pro Pro Cys
            20
```

(2) INFORMATION FOR SEQ ID NO:14:

(i) SEQUENCE CHARACTERISTICS:
        (A) LENGTH: 19 amino acids

```
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:14:

Met Lys Ala Ile Phe Val Leu Lys Gly Ser Leu Asp Arg Asp Leu Glu
1               5                   10                  15

Phe Met Cys
```